United States Patent [19]

Bassam et al.

[11] Patent Number: 5,413,909
[45] Date of Patent: May 9, 1995

[54] METHOD FOR PROFILING NUCLEIC ACIDS OF UNKNOWN SEQUENCE USING ARBITRARY OLIGONUCLEOTIDE PRIMERS

[75] Inventors: Brant J. Bassam; Gustavo Caetano-Anolles; Peter M. Gresshoff, all of Knoxville, Tenn.

[73] Assignee: The University of Tennessee Research Corp., Knoxville, Tenn.

[21] Appl. No.: 6,380

[22] Filed: Jan. 19, 1993

Related U.S. Application Data

[63] Continuation of Ser. No. 573,627, Aug. 24, 1990, abandoned.

[51] Int. Cl.⁶ .............................................. C12Q 1/68
[52] U.S. Cl. ..................... 435/6; 435/91.1; 435/91.2; 436/501; 536/24.3; 536/24.33
[58] Field of Search .................... 435/6, 91, 91.1, 91.2; 436/501; 536/22.1-24.33; 935/77, 88, 78

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 5,043,272 | 8/1991 | Hartley | 435/91 |
| 5,102,785 | 4/1992 | Livak et al. | 435/6 |
| 5,126,239 | 6/1992 | Livak et al. | 435/6 |

OTHER PUBLICATIONS

*New Riverside University Dictionary* (the Riverside Publ. Co., Boston Mass. 1984) p. 973.
Engelke et al., Proc. Natl Acad Sci USA, 85:544–548 (1988).
Wong et al. Nature, 330:384–386 (1987).
Botstein et al., Am. J Hum. Genet., 32:314–331 (1980).
White et al., Sci Am 258:40–48 (1988).
Jeffreys, Cell 18:1–10 (1979).
Proudfoot et al. Science 209:1329–2336 (1980).
Skolnick and Wallace, Genomics 2:273–278 (1988).
Dear and Cook, Nucleic Acids Research, 17:6795–6807 (1989).
Murray et al., Nucleic Acids Research vol. 8, No. 19, pp. 4321–4325 (1980).
Molecular Biology of Plants—Lab Manual pp. 36–37 (1984) (Cold Spring Harbor Laboratory, Cold Spring Habor, N.Y.).

*Primary Examiner*—Margaret Parr
*Assistant Examiner*—Ardin H. Marschel
*Attorney, Agent, or Firm*—Weiser & Associates

[57] ABSTRACT

A method for amplifying nucleic acid sequences in a template comprising at least one nucleic acid or mixture of nucleic acids wherein each nucleic acid comprises at least one strand. The method comprises the steps of treating the template with at least one oligonucleotide primer having a nucleic acid sequence that is substantially complementary to at least one nucleic acid sequence on the template under conditions such that the primer will bind to a segment that is substantially complementary to the primer, producing primed strands of nucleic acid. The primed strands produce extension strands, wherein the extension strands comprise the primer in combination with a sequence of nucleic acids that is substantially complementary to the template in a 5' to 3' direction from the primer. The extension strands are further treated with the primer producing amplification strands which are treated with primer. The amplification strands are repeatedly treated with primer to produce large numbers of amplification strands whereby the nucleic acid sequences of the amplification strands are substantially similar to nucleic acid sequences in the original template.

20 Claims, 4 Drawing Sheets

METHOD FOR PROFILING NUCLEIC ACIDS OF UNKNOWN SEQUENCE USING ARBITRARY OLIGONUCLEOTIDE PRIMERS

This is a continuation, of application Ser. No. 07/573,627, filed Aug. 24, 1990, now abandoned.

The present invention relates to a process for amplifying nucleic acid sequences present in a sample of nucleic acid and the detection of those nucleic acid sequences. More specifically, the present invention relates to a process for producing characteristic but unspecified sequences from a given sequence of nucleic acids in amounts which are large compared to the amount initially present. The process of the invention utilizes a repetitive reaction to accomplish the amplification of the desired nucleic acid sequence.

DNA profiling, also known as DNA "fingerprinting", has become a significant technology for the study of the human genome, linkage analysis, genetic predisposition to disease, parentage testing and genetic variation, and a powerful identification tool in forensic medicine and epidemiology. In an early technique of DNA fingerprinting restriction enzymes are used to cut sample DNA into millions of pieces, including fragments that contained repeated segments. The fragments produced are then separated by gel electrophoresis. Using this technique, the concentrations of the fragments are so low that they must be identified with a cloned radioactive probe. Since the probe is designed to identify only one particular sequence of nucleic acid, only a few of the millions of segments are identified. When the autoradiograph is developed, the resulting bands produce restriction fragment length polymorphisms (RFLP). Where there is a difference between the length of the fragments produced by the restriction enzyme those fragments are considered to be polymorphous. The polymorphous and non-polymorphous fragments are used to determine whether or not two samples belong to the same organism. Although this technique is widely used, the technology requires considerable DNA manipulation and is dependent upon the availability of cloned DNA probes to identify differences between fingerprints.

The polymerase chain reaction (PCR) is a key procedure for molecular biology research which has also been used for DNA fingerprinting. The PCR technique is an in vitro method in which a genomic or cloned target sequence is enzymatically amplified as directed by a pair of highly specific oligonucleotide primers. The amplification results from a repetitive reaction which produces large amounts of target sequence DNA when compared to the amount initially present in the DNA sample. PCR relies on stringent DNA hybridization and enzymatic reaction conditions as well as absolute primer specificity. In addition the PCR reaction requires two unique primers, each typically over twenty base pairs in length, for the amplification of a single target sequence.

It is an object of the present invention to provide a method for the amplification of unspecified but characteristic sequences of DNA. It is an object of the invention to provide this amplification without the DNA manipulation required by the RFLP technique or the specificity of the PCR technique. It is another object of the invention to provide a relatively simple method for profiling the DNA of an organism.

The present invention provides a method for amplifying nucleic acid sequences in a template comprising at least one nucleic acid or mixture of nucleic acids, wherein each nucleic acid comprises at least one strand having one 3' end and one 5' end. The method comprises the steps of first treating the template with at least one oligonucleotide primer having a nucleic acid sequence that is substantially complementary to at least one nucleic acid sequence on the template under conditions such that the primer will bind to a segment of the template that is substantially complementary to the primer, producing primed strands of nucleic acid. Next, the primed strands produce extension strands of nucleic acid wherein the extension strands comprise the primer in combination with a sequence of nucleic acids that is substantially complementary to the template in a 5' to 3' direction from the primer. The extension strands are then treated with the primer producing amplification strands of nucleic acid. The amplification strands are also treated with the primer to produce further amplification strands. The treatment of the amplification strands with primer is repeated a number of times to produce large numbers of amplification strands. The nucleic acid sequences of the amplification strands are substantially similar to nucleic acid sequences in the original template. Therefore, the amplified segments of nucleic acid are representative of the nucleic acid sample.

The process may be carried out in a single vessel for each sample of nucleic acid. The sample of nucleic acid and resulting amplified strands of nucleic acid are repeatedly separated by heating. Upon cooling, primer sequences attach to complementary nucleic acid sequences in solution. A polymerase then allows the formation of a complementary strand of nucleic acid synthesized in the 5' to 3' direction from the primer along the nucleic acid strand. After a short period of time, the temperature of the solution is again raised in order to denature the nucleic acid strands forms. This repetitive cycle provides large numbers of nucleic acid sequences which are the same as segments in the original sample nucleic acid.

The resulting nucleic acid strands are subjected to gel electrophoresis for separation by size. The distribution of amplified segments along the length of the gel represents a unique picture of the nucleic acid sample.

The primers used in the invention range in size from greater than five nucleotides. Primers less than five nucleotides in length generally do not produce recognizable fragments for nucleic acid fingerprinting. There is no specific required sequence for any particular primer used in this technique. Any sequence of nucleotides may be used as a primer so long as the same sequence is used when comparing different DNA samples. The fingerprint produced by a particular primer sequence will be unique to that sequence and will be repeatable when using this method with the same sample at two different times.

The present invention has the added advantage of not requiring narrowly specific reaction conditions. The present invention will produce repeatable and distinguishable fingerprints under a wide range of temperature conditions. The reaction mixture may be heated to as high as 98° C. and allowed to cool to as low as room temperature. A typical reaction involves 30–50 cycles of 1 sec. at 95° C., 10 sec. at 30° C. and 3 min. at 72° C.

In addition to fragments prepared according to the present invention, the amplified fragments may be further treated using restriction enzymes to produce subfragments which may be used for further identification of particular nucleic acid sequences.

The present invention may be better understood by reference to the following detailed description of the invention when considered in conjunction with the drawings in which.

Figures 1, 1A, 1B:
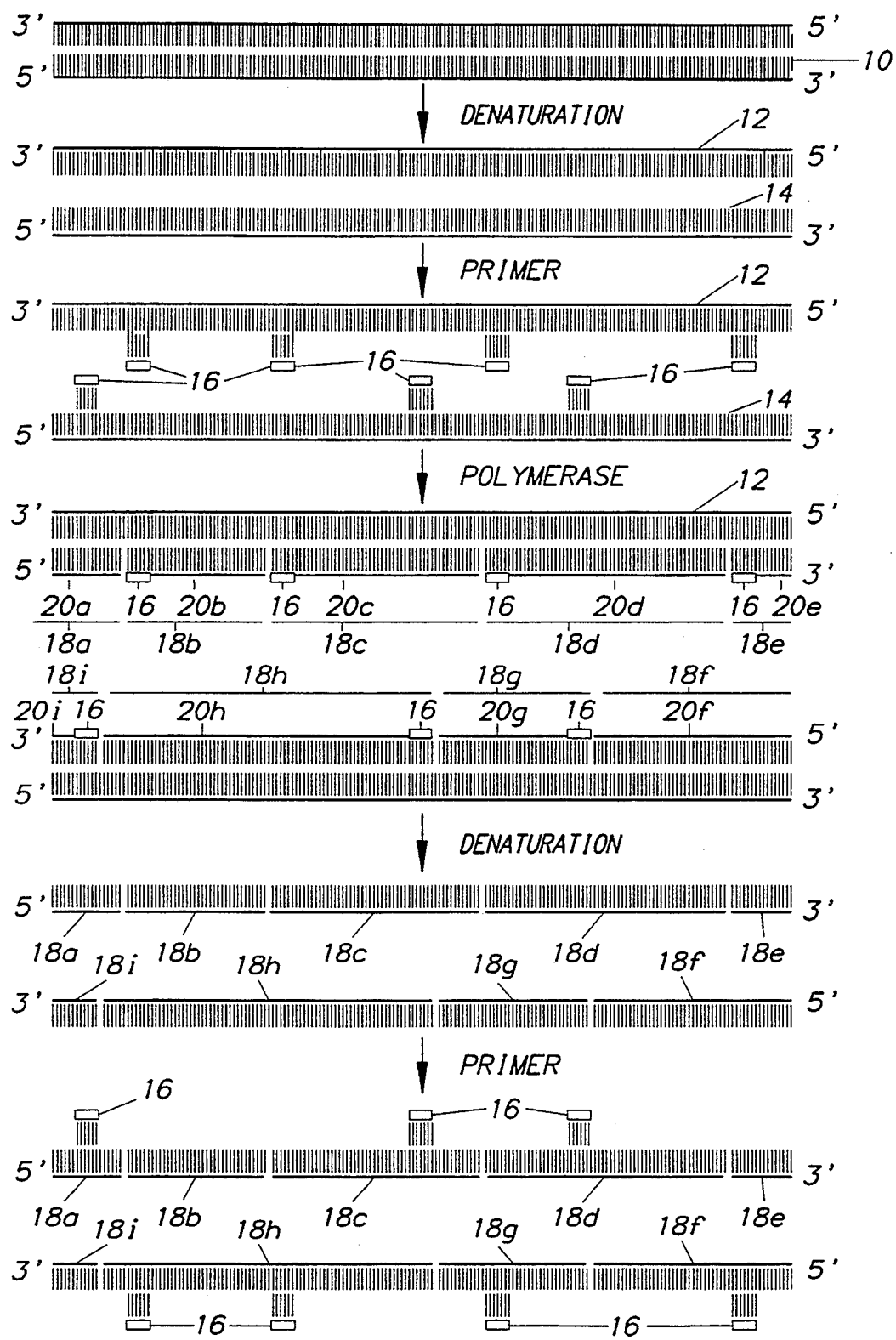
FIG. 1 is a diagram depicting the method of the present invention.
Figure 1B:
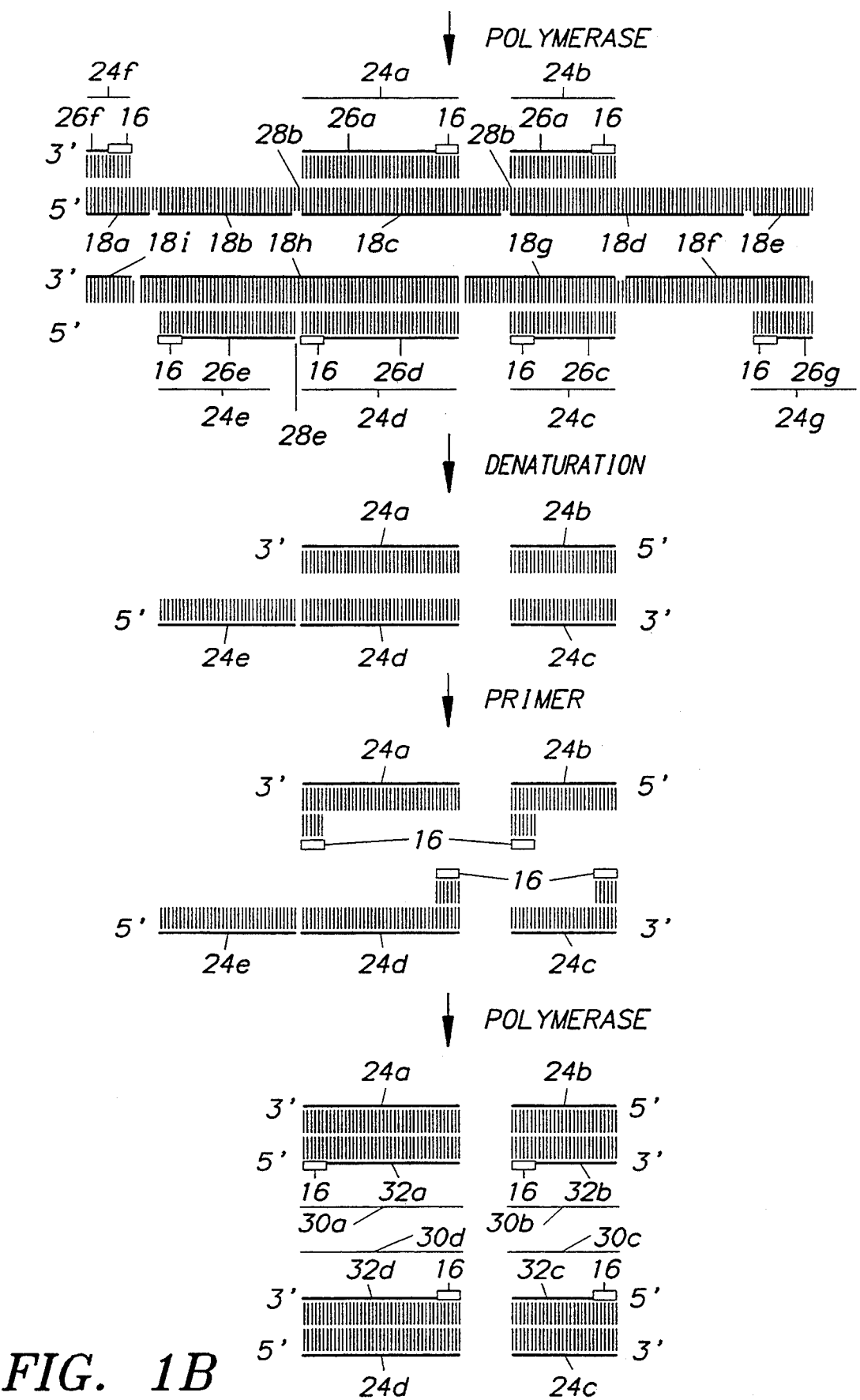

Referring now to FIG. 1, the method of the present invention is used with an original sample of DNA isolated by any one of a number of methods known in the art (e.g., R. H. Chesney, J. R. Scott and D. J. Vapnek, *J. Mol. Biol.*, vol. 130, pp. 161-173 [1979]). The original template of nucleic acid 10 is denatured to form two complementary strands 12 and 14. The complementary strands 12 and 14 are treated with a primer 16 comprising generally between 5 and 25 nucleotides. Primers of less than 5 nucleotides in length generally do not produce recognizable fragments for profiling. Primers of greater than about 25 nucleotides generally produce an insufficient number of amplified segments unless a particular nucleotide sequence is utilized. The sequence of the nucleotides is known but it is not important to the present invention that the sequence be complementary to a particular known segment on the template nucleic acid 10. The primer attaches to the complementary strands 12 and 14 at sites which are complementary to the nucleotides comprising the primer 16, forming primed complementary strands. The primed complementary strands are treated with a nucleic acid polymerase thereby generating extension strands of nucleic acid 18a-18i. The extension strands 18a-18i comprise a primer segment 16 in combination with a sequence 20a-20i of nucleic acids that is substantially complementary to the section of the complementary strands of nucleic acid 12 and 14. Each extension strand 18a-18i extends along the complementary strand 12 or 14 from the 5' end toward the 3' end of the extension strand 18a-18i. The extension strands 18a-18i have a length, as a maximum, of from its own primer 16 to a point 22a-22g just prior to the next primer 16 in the 3' direction. The DNA is then denatured and the extension strands 18a-18i are treated with additional primer 16 forming primed extension strands where the primer 16 is attached to the extension strands 18a-18i at sites which are complementary to the primers 16. Treatment of the primed extension strands with a nucleic acid polymerase produces amplification strands 24a-24g of nucleic acid, each strand 24a-24g comprising a primer 16 in combination with a sequence 26a-26g of nucleic acids that is substantially complementary to the section of the extension strands 18a-18i. The amplification strands 24a-24g are generated by the polymerase in the direction of the 3' end of the amplification strands 24a-24g and will be generated to the 5' end 28a-28e of any segment of an extension strand 18a-18i. For example, amplification strand 24a is generated to the 5' end 28a of extension strand 18c. The nucleic acid is then denatured producing free amplification strands 24a-24g. The amplification strands 24a-24g are treated with primer 16 forming primed amplification strands. Further treatment of the primed amplification strands with a nucleic acid polymerase produces additional amplification strands 30a-30d, each strand 30a-30d comprising a primer 16 in combination with a sequence 32a-32d of nucleic acids that is substantially complementary to the amplification strand 24a-24d. The amplification strand 24a is the complement of the amplification strand 30a, the amplification strand 24b is the complement of the amplification strand 30b and so forth. In this way, particular segments of nucleic acid are made available for further reproduction. The steps of denaturation, treating with primer 16 and treating with polymerase are repeated. Each further treatment will double the number of amplification strands 24a-24d and 30a-30d leading to a logarithmic increase in the number of amplification strands available for analysis. In the actual practice of the present invention, the repetitive reaction of denaturation, followed by primer treatment, followed by polymerase treatment is accomplished by combining the original nucleic acid sample with excess primer and nucleotides and the cycling of the reaction vessel through changes in temperature.

Figure 2:
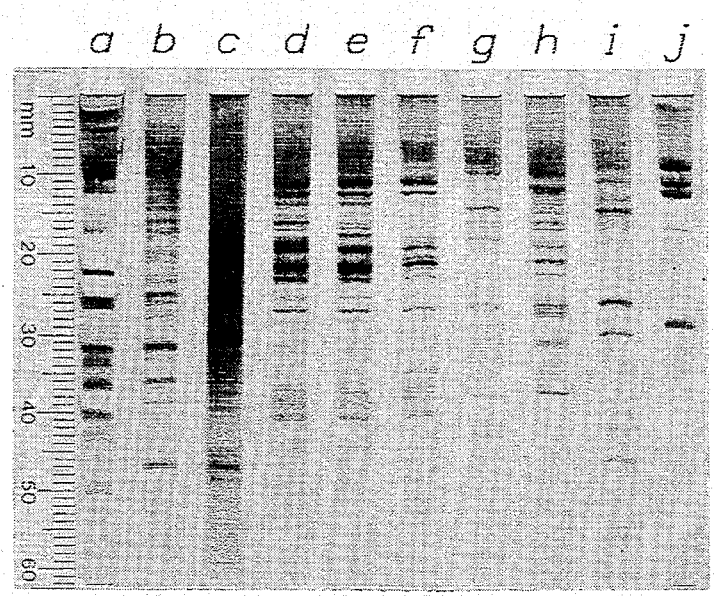
FIG. 2 depicts an electrophoresis gel which includes nucleic acid profiles from several different species using the primer with a sequence of 5'-CGCGGCCA-3' demonstrating the profiling capability of the present invention.
Figure 3:
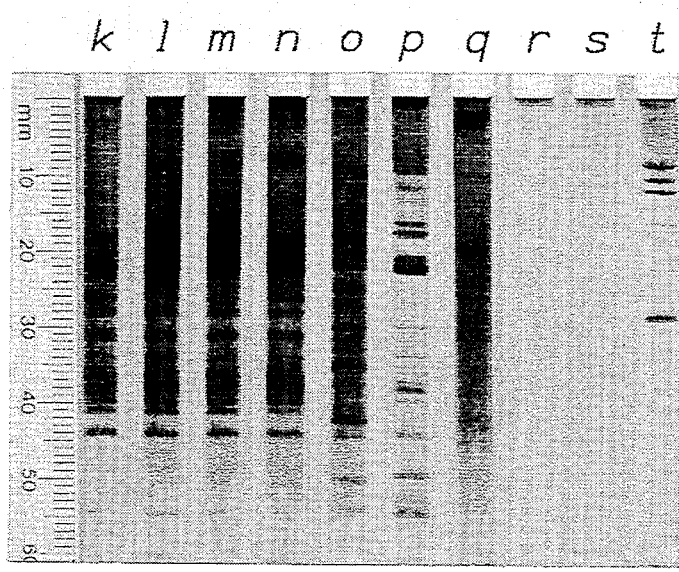
FIG. 3 depicts an electrophoresis gel which includes DNA profiles of the soybean *Glycine max* cv. Bragg using primers of different lengths and sequences.

Upon completion of the amplification of the nucleic acid fragments, the fragments are separated by gel electrophoresis and visualized, as with a silver stain. FIG. 1 illustrates the production of two different strands which are amplified by the method of the present invention. However, in operation, a large number of strands will be amplified, separated and visualized as is illustrated in FIGS. 2 and 3.

The primers are greater than five nucleotides in length. Preferentially, the primers are about ten nucleotides in length. Primers with fewer than five nucleotides do not produce amplified fragments necessary for DNA profiling. Primers much larger than about 25 nucleotides produce insufficient amplified segments unless a particular nucleotide sequence is utilized. Although a particular nucleotide sequence may be used according to the method of the present invention, it is not necessary to use a particular nucleotide sequence for the primers of the present invention. It is necessary, however, to use the same primer when comparing different samples for polymorphisms.

In order to provide a further understanding of the invention, the following examples are given primarily for the purposes of illustrating certain more specific details thereof.

EXAMPLE

Nucleic acid samples were obtained according to established procedures (e.g., R. H. Chesney, J. R. Scott and D. J. Vapnek, *J. Mol. Biol.*, vol. 130, pp. 161-173 [1979], S. L. Dellaporta, J. Wood and J. B. Hicks, *Plant Mol. Biol. Reporter*, vol. 1, pp. 19-21 [1983] and A. J. Jeffreys, V. Wilson and S. L. Thein, *Nature*, vol. 314, pp. 67-73 [1985]). Amplification was done in a total volume of 100 $\mu$l with 10-20 pg of sample nucleic acid, 1 $\mu$g of primer (an oligonucleotide of 5-9 nucleotides) and 2.5 units of a nucleic acid polymerase (AmpliTaq DNA polymerase from Perkin-Elmer/Cetus) in a reaction buffer comprised of 10 mM Tris-HCl (pH 8.3), 50 mM KCl, 2.5 mM $MgCl_2$ and 0.01% (w/v) gelatin (from Sigma). Deoxyribonucleoside triphosphates (dATP, dCTP, dGTC, dTTP) are also added to the reaction buffer at a concentration of 200 $\mu$M each. The reaction mix was overlayed with 2 drops of mineral oil, incubated for 5 minutes at 95° C. and amplified in a thermocycler from (Ericomp) connected to a refrigerated water bath for 30–50 cycles consisting of 1 sec at 95° C., 10 sec at 30° C. and 3 minutes at 72° C. The heating and cooling rates of the thermocycler were 23°/min. and 14°/min. respectively. Sample temperature was continuously monitored with a thermal probe. Amplification fragments were separated by polyacrylamide gel electrophoresis using a Mini-Protean II (from Bio-Rad) with 0.45 mm thick slab gels of 5% acrylamide and 7M urea (from Bio-Rad) with a ratio of acrylamide to piperazine diacrylamide (from Bio-Rad) 20:1. Gels and running buffer were prepared from TBE buffer comprising 100 mM Tris-HCl, 83 mM boric acid and 1 mM Na₂EDTA at pH=8.0. Electrophoresis was conducted at 70 V until the dye front (xylene cyanol FF) reached the bottom of the gel. The bands of nucleic acid fragments were visualized by silver staining according to D. Goldman and C. R. Merril, *Electrophoresis*, vol. 3, pp. 24–26 (1982).

FIG. 2 shows the DNA profiles of several different species using a single primer with a sequence of 5'-CGCGGCCA-3' wherein the nucleic acids of different organisms treated with the same primer produce varying patterns. Each organism produces a different series of bands after the amplification process of this invention. For example, experiment b shows the pattern of the nucleic acid of a caucasian human which is distinctly different from all other patterns shown in FIG. 2. However, comparison of experiments d, e and f show that closely related species may also be identified. Experiments d–f show the DNA profiles of soybeans. Experiments d and e are of the species *Glycine max* and experiment f shows the profile of the soybean *Glycine soja*. It is clear, from the number of polymorphous bands, that *G. max* and *G. soja* are related. However, it is also clear that the nucleic acids of experiments d and e are more closely related to each other than they are to the nucleic acid of experiment f. Experiment d used the cultivar Bragg where experiment e used the cultivar Peking. These two cultivars show many polymorphous bands but there are also nonpolymorphous bands as well. In this way, it is possible to distinguish two cultivars of the same species.

FIG. 2 also shows that the technique of the present invention is applicable to a wide range of organisms. Experiment b uses DNA from mammalian tissue where experiments c–h utilize plant tissue and experiment i uses DNA from a phage. Table I shows the specifics of experiments a–i.

TABLE I

| Experiment | Organism | Comment |
| --- | --- | --- |
| a | Hae III digest of phage X174 | Size Standard |
| b | caucasian human | — |
| c | *Cornus Florida* cv. Barton | Dogwood |
| d | *Glycine max* cv Bragg | Soybean |
| e | *Glycine max* cv. Peking | Soybean |
| f | *Glycine soja* PI 468.397 | Soybean |
| g | bermudagrass | — |
| h | centipedegrass | — |
| i | lambda phage c1857sam7 | — |
| j | Bst NI digest of plasmid pBR322 | SIZE standard |

FIG. 3 shows the profiles of a single species of soybean, *G. max* cv. Bragg, using primers of different lengths and sequences. Experiments k–n show the repeatability of the technique when applied to different samples from the same cultivar. All four samples were treated with the primer CGCGGCCA and there is no visible difference between the four profiles. In addition, experiments o–q show the profiles with primers different from that used in experiments k–n. Experiments r and s show that tetrameric primers do not produce the bands necessary for nucleic acid profiling according to the present invention. The details of the profiles shown in FIG. 3 are given in Table II.

TABLE II

| Experiment | Primer (5'–3') | Comment |
| --- | --- | --- |
| k | CGCGGCCA | 8-mer |
| l | CGCGGCCA | 8-mer |
| m | CGCGGCCA | 8-mer |
| n | CGCGGCCA | 8-mer |
| o | CGGCGGCGG | 9-mer |
| p | AATGCAGC | 8-mer |
| q | CCTGT | 5-mer |
| r | ACGT | 4-mer |
| s | GCGC | 4-mer |
| t | (Bst NI digest of plasmid pBR322) | SIZE standard |

From the above it may be seen that the present invention provides a method for the amplification of unspecified but repeatable sequences of DNA. Further, the invention provides this amplification without the DNA manipulation required by the RFLP technique or the specificity of the PCR technique. Further, the invention provides a relatively simple method for profiling the DNA of an organism. In addition, the invention may be applied to a wide range of organisms using a wide range of primers.

Various features of the invention which are believed to be new are set forth in the appended claims.

What is claimed is:

1. A method for generating a pattern characteristic of at least one nucleic acid of unspecified sequence in a sample, which method comprises:
   a) treating said nucleic acid with at least one oligonucleotide primer having an arbitrary sequence and of 5 to 25 nucleotides in length, the amount of primer being in excess over the amount of said nucleic acid, the amounts being in mass and allowing said primer to anneal to multiple sites on each strand of said nucleic acid, each site being substantially complementary to the nucleotides of which said primer is constituted, thus forming a multiplicity of a set of primed templates,
   b) treating said primed templates with a nucleic acid polymerase, thereby generating a multiplicity of extension strands, the extension strands comprising the primer in combination with a sequence of nucleotides that is substantially complementary to the templates, and extending along the template strands to either the 5' end of the template strands or the next primed site on the template, the number of extension strands thereby corresponding substantially to the number of primed sites,
   c) denaturing the extension strands from the template strands, thereby generating corresponding single-stranded extension strands and templates,
   d) allowing said primer to anneal to the extension strands and to the template strands,
   e) repeating steps (a), (b), (c) and (d) until there are generated nucleic acid fragments which are characteristic and unique for said nucleic acid of unspecified sequence,
   f) separating said fragments, and g) determining the characteristic pattern of fragments generated from said sequence of nucleic acid in the sample.

2. The method of claim 1 which comprises comparing the pattern resulting from step (g) with the pattern of fragments from another sequence of nucleic acid generated in (g) using a primer of the same sequence, thereby determining any difference and/or similarity between the two patterns of fragments by size.

3. The method of claim 1 wherein the primer is selected from the group consisting of primers of 5 to 10 nucleotides in length.

4. The method of claim 3 wherein the primer is selected from a group consisting of primers of 5, 8, 9 and 10 nucleotides in length.

5. The method of claim 2 wherein the sequence of the primer is known.

6. The method of claim 2 wherein the amount of primer is from 50,000 to 100,000 times that of the nucleic acids.

7. The method of claim 2 wherein the sample is a sample of mammalian tissue.

8. The method of claim 2 wherein the sample is a sample of plant tissue.

9. The method of claim 2 wherein the identification of the pattern is performed on a polyacrylamide gel.

10. A method for generating a pattern characteristic of at least one nucleic acid of unspecified sequence in a sample which method comprises:
  a) treating said nucleic acid with at least one oligonucleotide primer having an arbitrary sequence and of 8 nucleotides in length, the amount of primer being in excess over the amount of said nucleic acid, the amounts being in mass, and allowing said primer to anneal to multiple sites on each strand of said nucleic acid, each site being substantially complementary to the nucleotides of which said primer is constituted, thus forming a multiplicity of a set of primed templates,
  b) treating said primed templates with a nucleic acid polymerase, thereby generating a multiplicity of extension strands, the extension strands comprising the primer in combination with a sequence of nucleotides that is substantially complementary to the templates, and extending along the template strands to either the 5' end of the template strands or the next primed site on the template, the number of extension strands thereby corresponding substantially to the number of primed sites,
  c) denaturing the extension strands from the template strands thereby generating corresponding single-stranded extension strands and templates,
  d) allowing said primer to anneal to the extensions strands and to the template strands,
  (e) repeating steps (a), (b), (c) and (d) until there are generated nucleic acid fragments which are characteristic and unique for said nucleic acid of unspecified sequence,
  f) separating said fragments, and
  g) determining the characteristic pattern of fragments generated from said sequence of nucleic acid in the sample.

11. The method of claim 10 wherein the amount of primer is from 50,000 to 100,000 times that of the nucleic acids.

12. The method of claim 10 wherein the sequence of the primer is known.

13. The method of claim 10 which comprises comparing the pattern resulting from step (g) with the pattern of fragments from another sequence of nucleic acid generated in (g) using a primer of the same sequence, thereby determining any difference and/or similarity between the two patterns of fragments by size.

14. The method of claim 13 wherein the determination of the characteristic pattern is performed on a polyacrylamide gel.

15. The method of claim 13 wherein the sample is a sample of mammalian tissue.

16. The method of claim 13 wherein the sample is a sample of plant tissue.

17. The method of claim 1 which comprises treating the generated nucleic acid fragments with a restriction enzyme to produce subfragments of said nucleic acid fragments.

18. The method of claim 10 which comprises treating the generated nucleic acid fragments with a restriction enzyme to produce subfragments of said nucleic acid fragments.

19. The method of claim 16 wherein the comparison is of two patterns generated for the nucleic acid from plant tissue from two different cultivars of the same plant species.

20. The method of claim 13 wherein the sample is a bacteriophage.

* * * * *